US010335930B2

(12) United States Patent
Cutler

(10) Patent No.: US 10,335,930 B2
(45) Date of Patent: Jul. 2, 2019

(54) SHAFT RATCHET RELEASE AND SEALING MECHANISM

(71) Applicant: Brian James Cutler, Rowland Heights, CA (US)

(72) Inventor: Brian James Cutler, Rowland Heights, CA (US)

(73) Assignee: Lomak Industrial Company Limited, Hong Kong (HK)

( * ) Notice: Subject to any disclaimer, the term of this patent is extended or adjusted under 35 U.S.C. 154(b) by 792 days.

(21) Appl. No.: 14/883,471

(22) Filed: Oct. 14, 2015

(65) Prior Publication Data

US 2016/0101508 A1  Apr. 14, 2016

Related U.S. Application Data

(60) Provisional application No. 62/063,898, filed on Oct. 14, 2014.

(51) Int. Cl.
*B25B 13/46* (2006.01)
*B25B 15/04* (2006.01)
*B25B 23/142* (2006.01)
*A61B 17/88* (2006.01)
*A61B 90/00* (2016.01)

(52) U.S. Cl.
CPC ............ *B25B 13/465* (2013.01); *B25B 15/04* (2013.01); *B25B 23/1427* (2013.01); *A61B 17/8875* (2013.01); *A61B 2090/031* (2016.02)

(58) Field of Classification Search
CPC ... B25B 13/465; B25B 15/04; B25B 23/1427; B25B 23/0064; B25B 21/00; B25B 23/141; A61B 2090/031; A61B 17/887
See application file for complete search history.

(56) References Cited

U.S. PATENT DOCUMENTS

| | | | | | |
|---|---|---|---|---|---|
| 2,786,377 | A | * | 3/1957 | Riess | B25B 23/141 464/35 |
| 4,238,978 | A | * | 12/1980 | Leone | B25B 13/466 464/35 |
| 5,239,875 | A | * | 8/1993 | Stasiek | B25B 23/141 73/862.21 |
| 8,365,641 | B2 | * | 2/2013 | Daglow | B25B 23/1427 81/467 |
| 9,877,764 | B2 | * | 1/2018 | Nino | A61B 17/8875 |
| 2012/0198972 | A1 | * | 8/2012 | Nino | B25B 15/04 81/471 |
| 2013/0205569 | A1 | * | 8/2013 | Nino | A61B 17/8883 29/460 |

(Continued)

*Primary Examiner* — Monica S Carter
*Assistant Examiner* — Danny Hong
(74) *Attorney, Agent, or Firm* — James A. Italia; Italia IP

(57) ABSTRACT

A torque wrench having a handle and an output shaft is disclosed. The output shaft may be constrained to turn only unidirectionally due to a ratchet. Rotation of the output shaft may be permanently disabled by an internal mechanism. Torque imposed on the output shaft may be limited by a torque responsive cam clutch. The handle forms or is part of an enclosure enclosing internal components such as the ratchet, the internal disablement mechanism, and the torque responsive cam clutch. A seal between the body and the output shaft prevents ingress and egress of lubricants and contamination between the inside of the body and the output shaft.

1 Claim, 5 Drawing Sheets

(56) References Cited

U.S. PATENT DOCUMENTS

2013/0226192 A1* 8/2013 Nino ................... B25B 13/466
  606/104
2015/0367487 A1* 12/2015 Nino ................. A61B 17/8875
  81/473

* cited by examiner

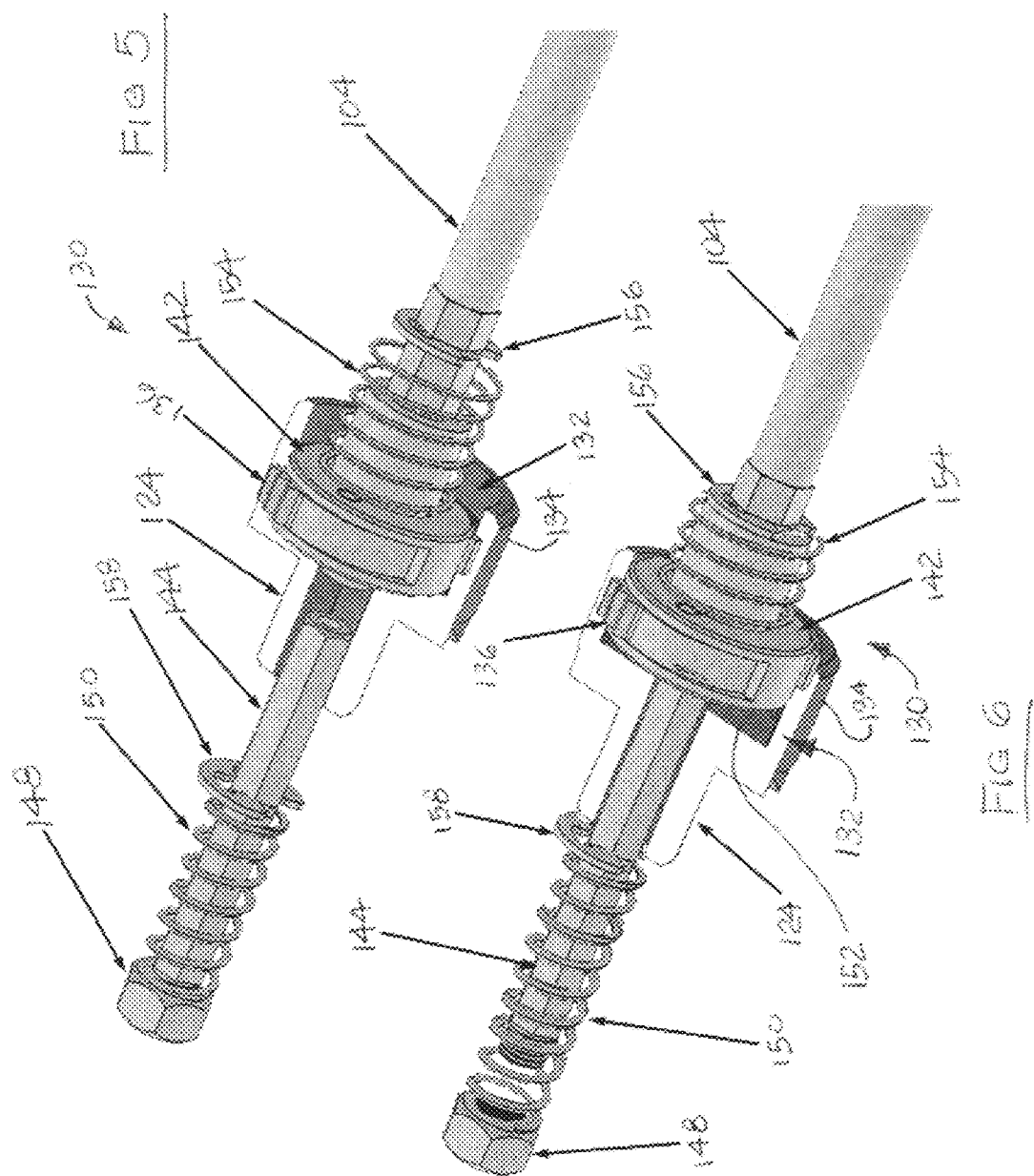

SHAFT RATCHET RELEASE AND SEALING MECHANISM

CROSS REFERENCE TO RELATED APPLICATIONS

This application claims the benefit of the filing date under 35 USC § 119(e) of U.S. Provisional Application Ser. No. 62/063,898, filed Oct. 14, 2014, the contents of which are incorporated herein by reference.

FIELD OF THE DISCLOSURE

The present disclosure relates to hand tools, and more particularly, to a torque wrench which has unidirectional functionality, and also can be rendered unserviceable automatically after a predetermined number of usages.

BACKGROUND

Tools for certain operations require a fairly high degree of precision. Illustratively, some operations require precise torque values to be applied to fasteners. One of the most effective ways to accomplish this goal is to provide a self-limiting torque wrench having a mechanism for limiting maximum applied torque. With such a mechanism, a user can freely turn the wrench without having to pay attention to the amount of torque being developed. Free turning of the wrench may entail alternating direction of wrench rotation, since that can be performed conveniently with one hand, without requiring that the hand be removed from the tool.

In some usages and environments, such a torque wrench can develop serious deficiencies. For example, in the field of high precision assembly, a torque wrench may go out of calibration to a degree unacceptable to assembly or fabrication standards. In another example, a torque wrench used in medical procedures such as installation of inserts in the human body may become internally contaminated, or may start to leak lubricant.

There exists a need for a torque wrench which overcomes the problems facing manually used wrenches.

SUMMARY

The disclosed concepts address the above stated situation by providing a manual torque wrench having a self-limiting torque feature and a feature which disables the wrench after a predetermined number of operations have been performed. The self-limiting torque feature may be based on an adjustable ratchet clutch mechanism in series with the torque delivery path. The disablement feature is based on internal components which cause a threaded end of a torque delivering shaft to progressively disengage from threading in the handle of the wrench over a predetermined number of usages of the torque wrench. Upon the torque delivering shaft becoming disengaged from the threading in the handle, an internal component of the wrench is moved to a position permanently disabling transmission of torque from the handle to an output shaft of the torque wrench.

It is an object to provide improved elements and arrangements thereof by apparatus for the purposes described which is inexpensive, dependable, and fully effective in accomplishing its intended purposes.

These and other objects will become readily apparent upon further review of the following specification and drawings.

BRIEF DESCRIPTION OF THE DRAWINGS

Various objects, features, and attendant advantages of the disclosed concepts will become more fully appreciated as the same becomes better understood when considered in conjunction with the accompanying drawings, in which like reference characters designate the same or similar parts throughout the several views, and wherein:

FIG. 5 is a perspective detail view similar to FIG. 4, but shown partially broken away to reveal internal detail, reflecting an engaged position of the subject components;

FIG. 6 is a perspective detail view similar to FIG. 5, but showing some components moved to a disengaged position.

DETAILED DESCRIPTION

Figure 1:
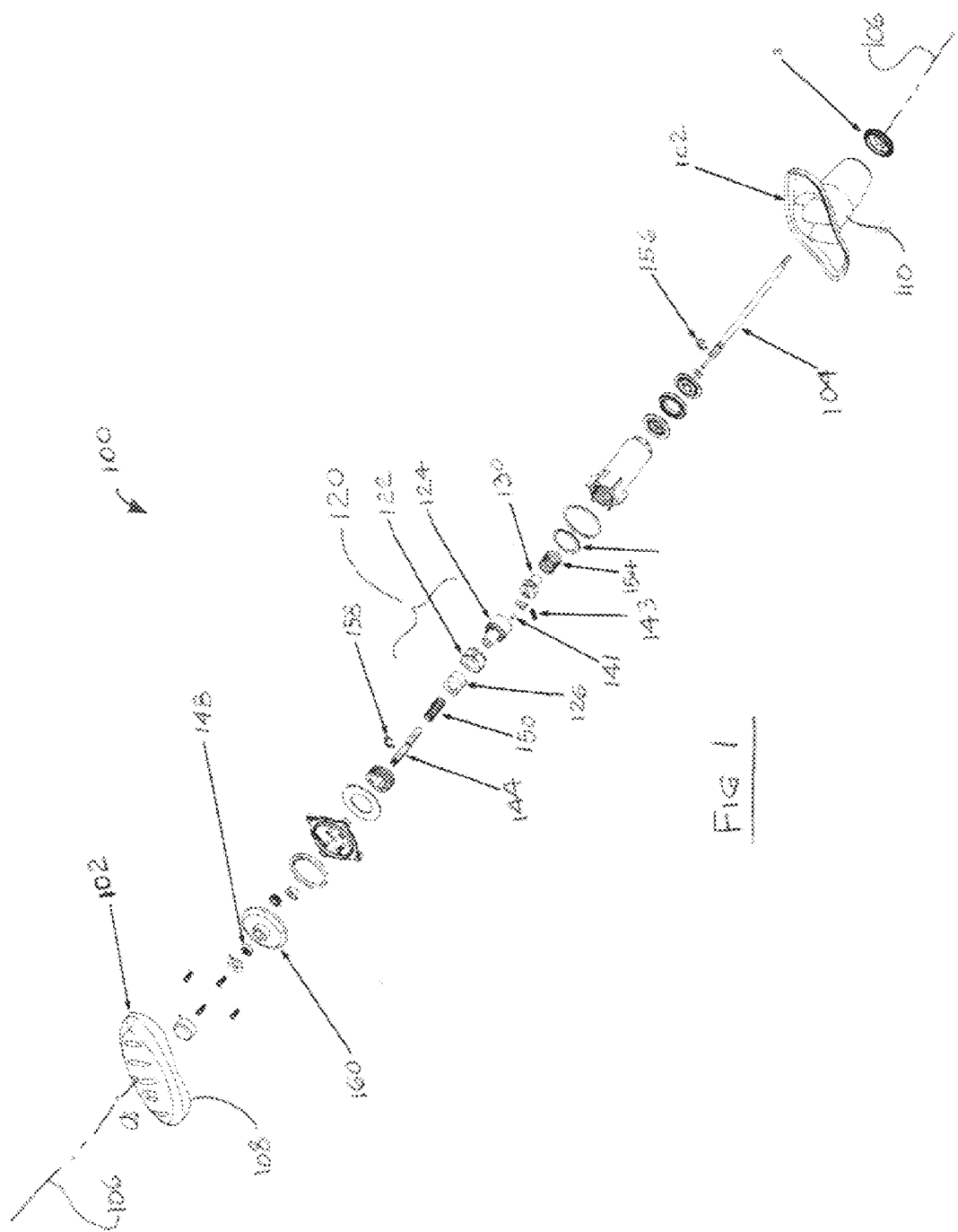
FIG. 1 is an exploded perspective view of a torque wrench, according to at least one aspect of the disclosure.

Referring first to FIG. 1, according to at least one aspect of the disclosure, there is shown a torque wrench 100 having a feature for permanently discontinuing ability to transmit torque. Torque wrench 100 comprises a handle 102 and an output shaft 104 coupled to, and driven by rotation of, handle 102. Output shaft 104 has an axis of rotation 106 about which output shaft 104 rotates when handle 102 rotates.

Torque wrench 100 may include a torque control (to be described hereinafter) responsive to torques imposed on output shaft 104 from handle 102, and may include a disengagement feature which becomes operable to permanently disconnect handle 102 from output shaft 104. Permanent disconnection of handle 102 from output shaft 104 enables torque wrench 100 to be utilized throughout a period of predictable accuracy and freedom from unreliability and other issues. When disengagement occurs, would be users of torque wrench 100 are obliged to select a relatively new torque wrench 100, and are thereby not susceptible to inaccurate torque settings and other problems resulting from an overused tool.

FIG. 1 shows components of one contemplated implementation of torque wrench 100, including components having little if any bearing on presently claimed features of torque wrench 100. These components are shown to further appreciation of the compact nature achieved in torque wrench 100, but are not identified by reference numeral or description. Further details regarding operation of torque wrench 100 and its components may be gleaned from U.S. Pat. No. 7,487,700, issued to Cutler et al. on Feb. 10, 2009, which patent is incorporated herein by reference.

Handle 102 comprises a handle cap 108 which complements a handle body 110. When mated together, handle cap 108 and handle body 110 of handle 102 form an enclosure which encloses all of the internal components of torque wrench 100, except for output shaft 104. Referring to FIGS.

1 and 3, in an example of torque wrench 100, handle 102 forms an enclosure from which output shaft 104 projects. Torque wrench 100 further comprises a seal 112 between output shaft 104 and handle 102. Seal 112 comprises a first resilient layer 114 and a second resilient layer 116 each spaced apart from one another along axis of rotation 106. First and second resilient layers 114, 116 are supported and may be permanently secured to an intervening structural member or holder 118.

Unless otherwise indicated, the terms "first", "second", etc., are used herein merely as labels, and are not intended to impose ordinal, positional, or hierarchical requirements on the times to which these terms refer. Moreover, reference to, e.g., a "second" item does not either require or preclude the existence of, e.g., a "first" or lower-numbered item, and/or, e.g., a "third" or higher-numbered item.

In an example of torque wrench 100, the torque control comprises a torque responsive clutch 120 which automatically disengages output shaft 104 from handle 102 upon attainment of a predetermined torque. Torque responsive clutch 120 is contained entirely within handle 102.

Figure 2:
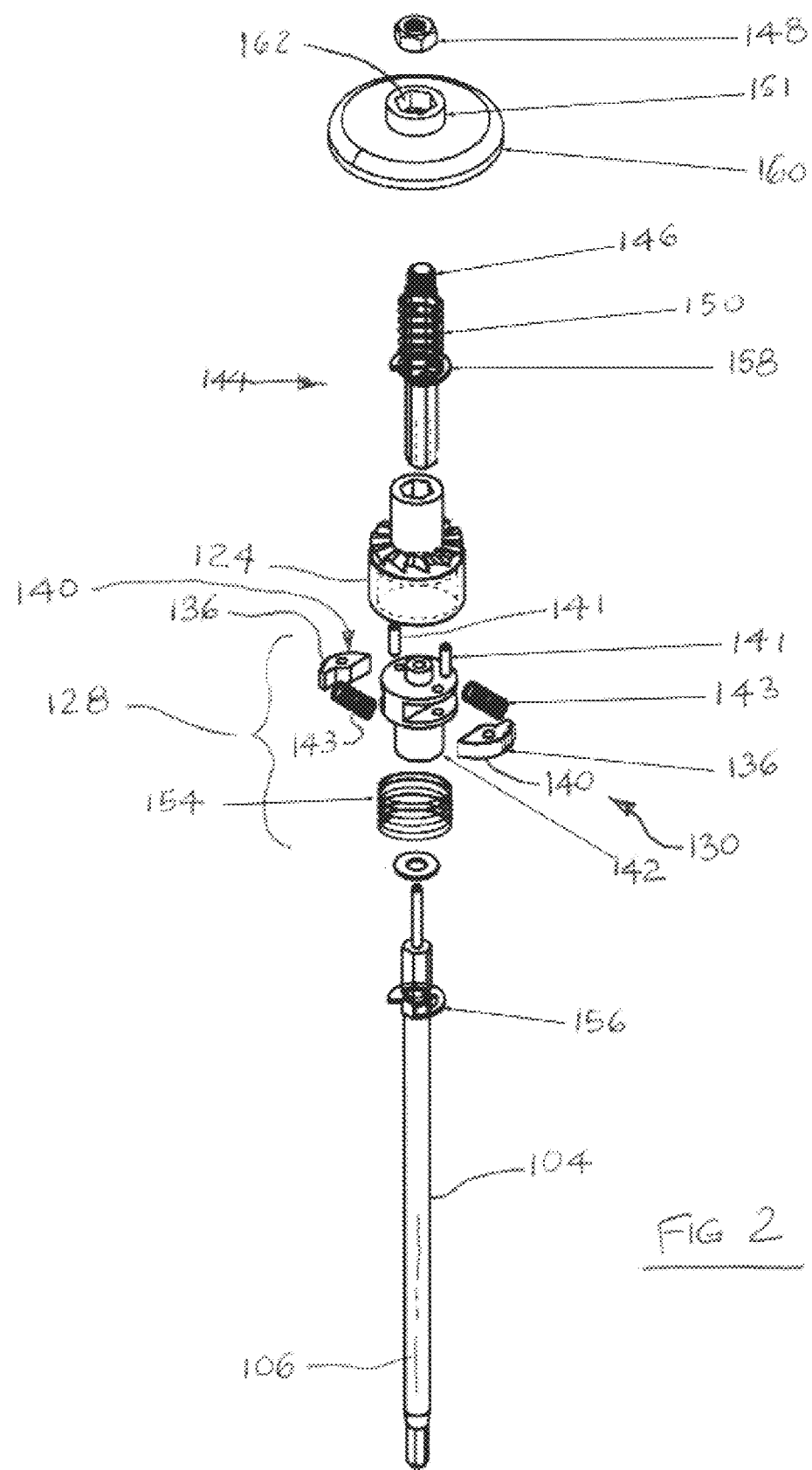
FIG. 2 is an exploded perspective detail view, showing only some of the components of FIG. 1, and is drawn to greater scale than FIG. 1.
Figure 3:
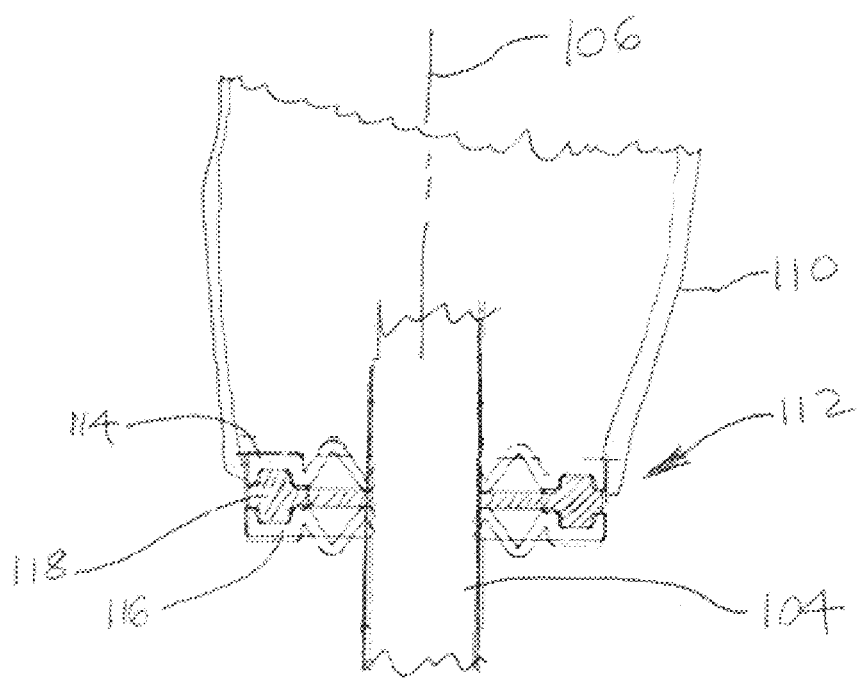
FIG. 3 is a side cross sectional view of some components shown at the lower end of FIG. 1, reflecting the assembled condition of the subject torque wrench, and drawn to enlarged scale.

Referring to FIGS. 1 and 2, torque responsive clutch 120 comprises opposed cams 122, 124, wherein opposed cams 122, 124 interfit with one another in a torque transmitting mode when transmitting torque. Opposed cams 122, 124 separate from one another in a released mode when not transmitting torque. A spring 126 urges opposed cams 122, 124 towards one another. As used herein, cams 122 and 124 will be understood to refer to a cam assembly including both the actual cam surfaces, and also additional structural members formed monolithically with the cam surfaces. Each cam 122, 124 has inclined ramps of known type of pitches enabling one cam 122 or 124 to rotate the other cam 124 or 122 until a predetermined threshold of torque is attained. This threshold is determined in part by spring 126. When torque increases above the threshold, cams 122 and 124 slide over the ramps of the other cam 124 or 122, thereby spacing cams 122, 124 apart axially (with respect to axis of rotation 106) until they are no longer able to rotate in tandem. When this happens, cam 122, which receives rotational input by rotating handle 102, rotates ineffectually, while cam 124 remains immobile.

This is a known torque limiting arrangement which is not novel per se. Providing this torque limiting arrangement enables the user to concentrate on rotating torque wrench 100, without the distraction of monitoring applied torques.

Although the torque limiting arrangement has been presented in terms of a device which decouples output shaft 104, the torque limiting arrangement could be instead a readout or other signaling arrangement which annunciates attainment of a predetermined torque value. Examples include a needle deflected by imposition of torque, taken together with a scale, or alternatively, an alphanumerical display.

In an example of torque wrench 100, the disengagement feature comprises a rotational coupling 128 between handle 102 and output shaft 104. Rotational coupling 128 is contained entirely within handle 102. This is one of several structural features of torque wrench 100 providing highly compact configuration.

In the example of FIGS. 1 and 2, rotational coupling 128 comprises a unidirectional ratchet 130 performing or contributing to two distinct functions. In one function, unidirectional ratchet 130 selectively enables output shaft 104 to rotate relative to handle 102 in a first direction when handle 102 is turned in the first direction about axis of rotation 106, and constrains output shaft 104 against rotating relative to handle 102 when handle 102 is turned in a second direction about axis of rotation 106 opposite the first direction. Therefore, torque wrench 100 can be operated using one hand, by alternating directions of rotation of handle 102, without obliging the user to remove his or her hand from handle 102.

As seen in FIGS. 2 and 4-6, in an implementation of torque wrench 100, unidirectional ratchet 130 is supported on and at least partially contained within rotational coupling 128. More specifically, and best seen in FIGS. 5 and 6, unidirectional ratchet 130 is received within a partially enclosed space 132 formed by a skirt 134 extending from cam 124. This results in a highly compact arrangement accommodating components providing several functions of torque wrench 100 within handle 102.

Looking particularly at FIGS. 5 and 6, unidirectional ratchet 130 has teeth 136 projecting radially outwardly relative to axis of rotation 106. Teeth 136 of unidirectional ratchet 130 engage corresponding grooves 138 (see FIG. 7) in rotational coupling 128. The disengagement feature displaces teeth 136 of unidirectional ratchet 130 axially out of engagement with corresponding grooves 138 of rotational coupling 128, thereby enabling output shaft 104 to rotate freely relative to handle 102.

Figure 7:
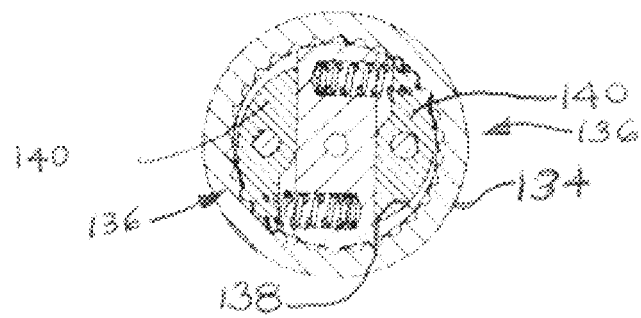
FIG. 7 is a bottom plan detail view taken along line 7-7 of FIG. 4.
Figure 4:
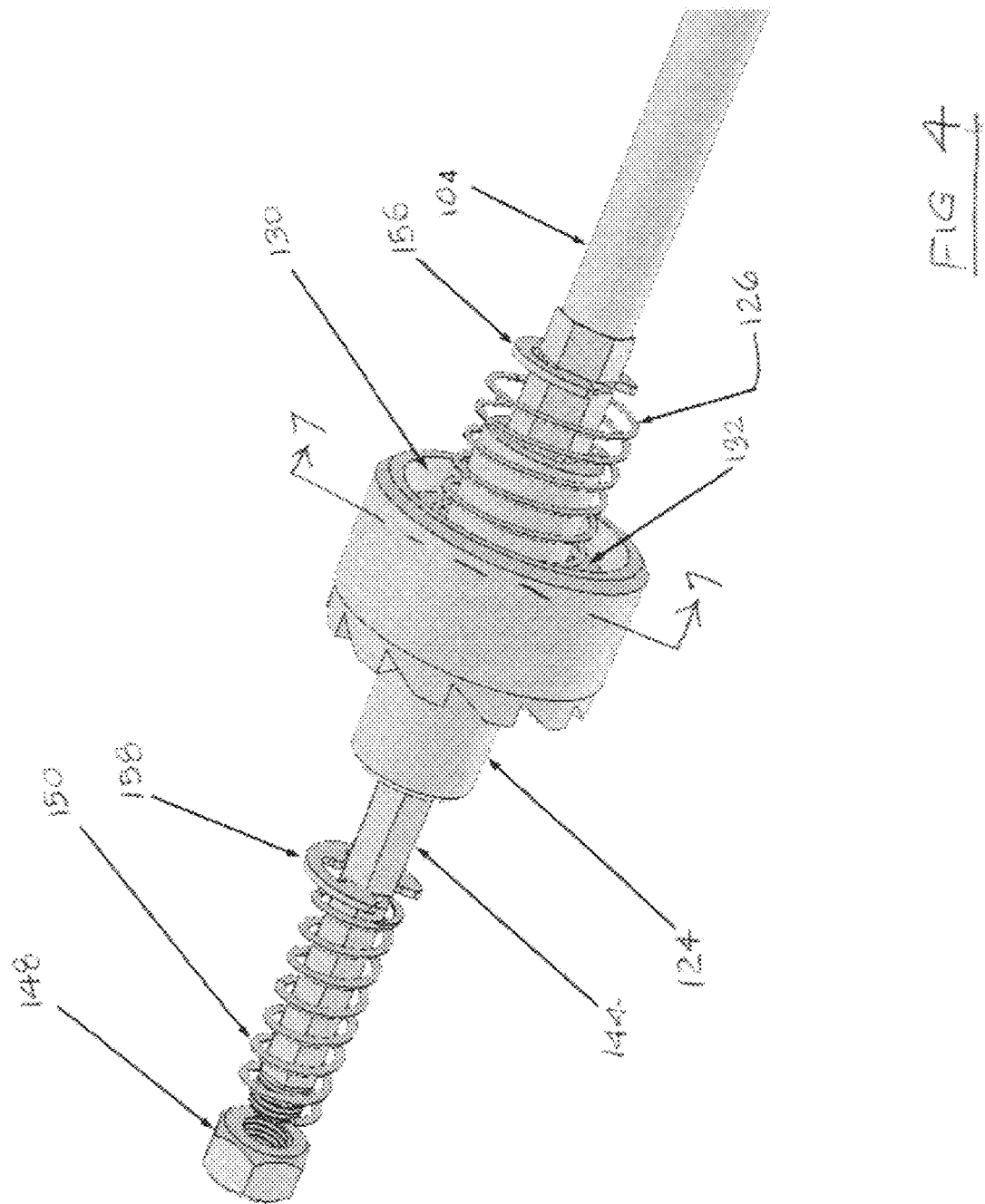
FIG. 4 is a perspective detail view of some components shown towards the center of FIG. 1, reflecting the assembled condition, and drawn to enlarged scale.

FIGS. 2 and 7 clarify the nature of unidirectional ratchet 130. Pawls or teeth 136 are mounted on two swing arms 140 pivotally mounted to a ratchet support member 142. Pins 141 (one representative pin 141 is shown in FIG. 1) pivotally support swing arms 140. Swing arms 140 are urged against the inner wall of skirt 134 by swing arm springs 143, which inner wall bears grooves 138. Teeth 136 and corresponding grooves 138 are configured such that when ratchet support member 142 is rotated in one direction about axis of rotation 106, the ratchet mechanism engages skirt 134 of cam 124, and torque is transmitted. When ratchet support member is rotated in an opposite direction, teeth 136 readily disengage from grooves 138, and no torque is transmitted. Configuration of teeth 136 and grooves 138 implies that pitch angles, rounding of contours, and the like of teeth 136 and grooves 138 favor slippage in one direction, but tend to oppose mutual slippage in the opposite direction.

Thus far, one of the two functions involving unidirectional ratchet 130 has been described, notably, effecting unidirectional rotation of output shaft 104 responsive to torque inputs imposed on handle 102. The second function is that of permanently disabling transmission of torque from handle 102 to output shaft 104. This latter function will now be described. Generally, permanent disablement can be accomplished by displacing ratchet support member 142 and its associated swing arms 140 and teeth 136 along axis of rotation 106, such that teeth 136 no longer align with associated grooves 138.

Turning now to FIG. 2, torque wrench 100 further comprises a push rod 144 operable to advance along rotational axis 106 within handle 102. Push rod 144 then contacts unidirectional ratchet 130, and displaces unidirectional ratchet 130 axially out of engagement with rotational coupling 128. Push rod 144 may be regarded as an upper section of output shaft 104, and plays a role in receiving torque and transmitting torque to output shaft 104 via rotational coupling 128 and unidirectional ratchet 130.

It should be noted at this point that orientational terms such as upper refer to the subject drawing as viewed by an observer. The drawing figures depict their subject matter in orientations of normal use, which could obviously change depending on how novel torque wrench 100 is held. Therefore, orientational terms must be understood to provide semantic basis for purposes of description only, and do not imply that their subject matter can be used only in one position.

In the example of FIGS. 1, 2, and 4-6, push rod 144 has threading 146. Handle 102 comprises a threaded inhibiting member 148 matingly compatible with threading 146 of push rod 144. Push rod 144 is initially threaded to threaded inhibiting member 148 of handle 102, and progressively unthreads from threaded inhibiting member 148 with each usage of torque wrench 100. Torque wrench 100 comprises a second spring 150 urging push rod 144 towards unidirectional ratchet 130. When push rod 144 is fully unthreaded from threaded inhibiting member 148, second spring 150 urges push rod 144 against unidirectional ratchet 130 such that unidirectional ratchet 130 is disengaged from rotational coupling 128 by displacing teeth 136 of unidirectional ratchet 130 axially out of engagement with grooves 138 of rotational coupling 128. FIG. 5 shows unidirectional ratchet 130 in the normal or engaged position. In FIG. 6, unidirectional ratchet 130 has been displaced downwardly, leaving visible an upper space 152 in the enclosed space 132 of cam 124. A third spring 154 holds unidirectional ratchet 130 in the normal position until acted on by push rod 144. Third spring 154 seats against a clip 156 secured to output shaft 104. Second spring 150 seats at one end against threaded inhibiting member 148 and at an opposed end at a clip 158 secured to push rod 144. Spring 150 has greater force than spring 154, so that unidirectional ratchet 130 will not spontaneously reassume the normal position shown in FIG. 5.

Threaded inhibiting member 148 is presented as a part of handle 102. In the implementations of torque wrench 100 presented herein, threaded inhibiting member 148 is depicted as a nut held within a hexagonally configured passage 162 of a projection 161 of a cap 160 which cap 160 is, in the assembled torque wrench 100, fixed to handle 102.

In the above description, numerous specific details are set forth in order to provide an understanding of the present invention. It will be apparent, however, to one skilled in the art that the present invention may be practiced without these specific details. In other instances, well known components or methods have not been described in detail but rather in a block diagram in order to avoid unnecessarily obscuring the present invention. Thus, the specific details set forth are merely exemplary. The specific details may be varied from and still be contemplated to be within the spirit and scope of the present invention.

While the disclosed concepts have been described in connection with what is considered the most practical and preferred implementation, it is to be understood that the disclosed concepts are not to be limited to the disclosed arrangements, but are intended to cover various arrangements which are included within the spirit and scope of the broadest possible interpretation of the appended claims so as to encompass all modifications and equivalent arrangements which are possible.

It should be understood that the various examples of the apparatus(es) disclosed herein may include any of the components, features, and functionalities of any of the other examples of the apparatus(es) disclosed herein in any feasible combination, and all of such possibilities are intended to be within the spirit and scope of the present disclosure. Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples presented and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims.

I claim:
1. A torque wrench having a feature for permanently discontinuing ability to transmit torque, comprising:
   a handle;
   an output shaft coupled to, and driven by rotation of, the handle, the output shaft having an axis of rotation about which the output shaft rotates when the handle rotates;
   a torque control responsive to torques imposed on the output shaft from the handle, wherein the torque control comprises a torque responsive clutch which automatically disengages the output shaft from the handle upon attainment of a predetermined torque, wherein the torque responsive clutch is contained entirely within the handle, wherein the torque responsive clutch comprises opposed cams, wherein
      the opposed cams interfit with one another in a torque transmitting mode when transmitting torque and
      the opposed cams separate from one another in a released mode when not transmitting torque, and
   a first spring urging the opposed cams towards one another;
   a unidirectional ratchet selectively enabling the output shaft to rotate relative to the handle in a first direction when the handle is turned in the first direction about the axis of rotation and constraining the output shaft against rotating relative to the handle when the handle is turned in a second direction about the axis of rotation opposite the first direction, wherein the unidirectional ratchet is supported on and at least partially contained within the rotational coupling, wherein the unidirectional ratchet
      has teeth projecting radially outwardly relative to the axis of rotation;
      the teeth of the unidirectional ratchet engage corresponding grooves in the rotational coupling;
   a push rod operable to advance along the rotational axis within the handle, contact the unidirectional ratchet, and displace the unidirectional ratchet axially out of engagement with the rotational coupling, wherein the push rod has threading, wherein said handle includes a threaded inhibiting member matingly compatible with the threading of the push rod, wherein the push rod is initially threaded to the threaded inhibiting member of the handle, and progressively unthreads from the threaded inhibiting member with each usage of the torque wrench;
   a second spring urging the push rod towards the unidirectional ratchet, whereby when the push rod is fully unthreaded from the threaded inhibiting member, the second spring urges the push rod against the unidirectional ratchet such that the unidirectional ratchet is disengaged from the rotational coupling by displacing the teeth of the unidirectional ratchet axially out of engagement with the grooves of the rotational coupling; and a disengagement feature which becomes operable to permanently disconnect the handle from the output shaft, wherein the disengagement feature displaces the teeth of the unidirectional ratchet axially out of engagement with the corresponding grooves of the rotational coupling, thereby enabling the output shaft to rotate freely relative to the handle.

* * * * *